US012710413B2

(12) United States Patent
Gao et al.

(10) Patent No.: US 12,710,413 B2
(45) Date of Patent: Aug. 18, 2026

(54) COLLECTION METHOD FOR PARTICULATE MATTER DETECTOR

(71) Applicant: ELITECH TECHNOLOGY, INC., San Jose, CA (US)

(72) Inventors: Zhao Gao, San Jose, CA (US); Ning Xue, San Jose, CA (US); Xiaofan Li, San Jose, CA (US); Tongsheng Sun, San Jose, CA (US)

(73) Assignee: ELITECH TECHNOLOGY, INC., San Jose, CA (US)

( * ) Notice: Subject to any disclaimer, the term of this patent is extended or adjusted under 35 U.S.C. 154(b) by 214 days.

(21) Appl. No.: 18/626,516

(22) Filed: Apr. 4, 2024

(65) Prior Publication Data

US 2025/0076269 A1 Mar. 6, 2025

(30) Foreign Application Priority Data

Aug. 28, 2023 (CN) ........................ 202311093707.7

(51) Int. Cl.
*G01N 33/00* (2006.01)
*G01N 1/22* (2006.01)

(52) U.S. Cl.
CPC ........... *G01N 33/0068* (2024.05); *G01N 1/22* (2013.01); *G01N 2001/2297* (2013.01)

(58) Field of Classification Search
None
See application file for complete search history.

(56) References Cited

U.S. PATENT DOCUMENTS

| | | | | |
|---|---|---|---|---|
| 9,121,837 | B2 * | 9/2015 | Chan | G01N 33/0032 |
| 2025/0146919 | A1 * | 5/2025 | Thomson | G01N 33/0039 |

FOREIGN PATENT DOCUMENTS

| | | | | |
|---|---|---|---|---|
| CN | 104422638 A | * | 3/2015 | G01N 15/06 |
| CN | 107064426 A | * | 8/2017 | G16Z 99/00 |

(Continued)

*Primary Examiner* — Peter J Macchiarolo
*Assistant Examiner* — Jermaine L Jenkins
(74) *Attorney, Agent, or Firm* — Birch, Stewart, Kolasch & Birch, LLP

(57) ABSTRACT

The present invention relates to a collection method for a particulate matter detector, including: performing normalized calculation on collected initial air particulate matter values, to calculate an initial particulate matter variation among the initial air particulate matter values; obtaining a real-time collection cycle coefficient by performing calculation on the initial particulate matter variation through a stepwise approximation method and table lookup, and calculating a real-time particulate matter collection interval time; then, collecting an air particulate matter value again after the real-time collection interval time, where the air particulate matter value collected at this time is a latest air particulate matter value; performing normalized calculation on the latest air particulate matter value and a data value displayed by the particulate matter detector, to calculate a real-time particulate matter variation; and obtaining a new real-time collection cycle coefficient by performing calculation on the real-time particulate matter variation through the stepwise approximation method and table lookup. According to the present invention, a particulate matter detector can adjust a collection interval time in real time as a concentration of particulate matters in the air changes, thereby improving an endurance capacity thereof.

10 Claims, 2 Drawing Sheets

(56) References Cited

FOREIGN PATENT DOCUMENTS

| | | | | |
|---|---|---|---|---|
| CN | 109141525 | A | | 1/2019 |
| JP | 2004028945 | A | * | 1/2004 |

* cited by examiner

COLLECTION METHOD FOR PARTICULATE MATTER DETECTOR

TECHNICAL FIELD

The present invention relates to the field of particulate matter detectors, and in particular, to a collection method for a particulate matter detector.

BACKGROUND

As people's living standards are increasingly improved, requirements on air quality are also increasingly high, especially a high degree of concern about a fine particulate matter (that is, PM 2.5). Compared with a coarser atmospheric particulate matter, the PM 2.5 has a smaller particle size, a larger area, and a stronger activity and is easier to carry a toxic and harmful substance (such as a heavy metal, a microorganism, and the like), and stays in the atmosphere for a long time and is transported over a long distance, which has a great impact on human health and quality of the atmospheric environment. Therefore, a portable particulate matter detector needs to be used in increasingly more scenarios for air quality monitoring.

In existing portable particulate matter detectors, a β ray method is usually used to measure a concentration of particulate matters, and the concentration of the particulate matters in the air is regularly detected.

However, in a process of detecting the particulate matters, a traditional particulate matter detector usually uses a fixed collection rate to collect air particulate matter data, and rarely uses a control method for adjusting a particulate matter collection rate according to a variation of the particulate matters in the air. In most cases, a change in the concentration of the particulate matters in the air is small. Since the particulate matters in the air are collected at a fixed collection rate, it is difficult to reduce the energy consumption of the portable particulate matter detector. A battery life of the traditional portable particulate matter detector generally ranges from 6 hours to 8 hours, which is difficult to meet usage requirements of a user. However, when the concentration of the particulate matters in the air changes frequently, since a fixed particulate matter collection rate is used, a quantity of times of collection of particulate matter concentration information in the air is relatively small, and the particulate matter concentration information in the air cannot be accurately collected.

SUMMARY

In view of the foregoing problems in the related art, the present invention aims to provide a collection method for a particulate matter detector that can adjust a particulate matter collection rate according to changes in a concentration of particulate matters in the air.

A collection method for a particulate matter detector, comprising the following steps:

S1, collecting N groups of initial air particulate matter values according to an initial collection duration $t_1$;

S2, performing normalized calculation on the collected N groups of initial air particulate matter values, to calculate an initial particulate matter variation $r_1$ among the initial air particulate matter values, and calculating an initial air particulate matter value $d_0$ according to the initial air particulate matter values;

S3, obtaining a real-time collection cycle coefficient $t_2$ by performing calculation on the initial particulate matter variation $r_1$ through a stepwise approximation method and table lookup;

S4, calculating a real-time particulate matter collection interval time $t_4$ according to the real-time collection cycle coefficient $t_2$ and a shortest collection interval time $t_3$ of the particulate matter detector;

S5, collecting an air particulate matter value again after the real-time collection interval time $t_4$, where the air particulate matter value collected at this time is a latest air particulate matter value $d_1$;

S6, performing normalized calculation on the latest air particulate matter value $d_1$ and a data value $d_0$ displayed by the particulate matter detector, to calculate a real-time particulate matter variation $r_2$;

S7, obtaining a new real-time collection cycle coefficient $t_2$ by performing calculation on the real-time particulate matter variation $r_2$ through the stepwise approximation method and table lookup, wherein the latest air particulate matter value $d_1$ is assigned to the initial air particulate matter value $d_0$ in this case; and S8, repeating the steps from S4 to S7.

Further, in S2, when N is an even number, the initial particulate matter variation $r_1$ is calculated using the following formula, $$r_1 = \left|\frac{a_1 - a_2}{a_1}\right|$$

in the formula, $a_1$ is an average value of the first N/2 groups of initial air particulate matter value data, and $a_2$ is an average value of the last N/2 groups of initial air particulate matter value data.

Further, in S2, when N is an odd number, a first piece of data in the N groups of data is discarded, M groups of data is left, and the initial particulate matter variation $r_1$ is calculated using the following formula, $$r_1 = \left|\frac{a_3 - a_4}{a_3}\right|$$

in the formula, $a_3$ is an average value of the first M/2 groups of initial air particulate matter value data, and $a_4$ is an average value of the last M/2 groups of initial air particulate matter value data.

Further, a specific method of the stepwise approximation method and table lookup in S3 and S7 is: defining the initial particulate matter variation $r_1$ or the real-time particulate matter variation $r_2$ as a variation r, setting a table, and dividing the variation r in the table into several variation segments b from 0 to 1, wherein each variation segment b has a different value range; each variation segment b is provided with a corresponding collection cycle segment c, and each collection cycle segment c also has a different value range; and a calculation formula using the stepwise approximation method is:

$$t_2 = \frac{t_{hi} - t_{lo}}{r_{hi} - r_{lo}}(r - r_{lo}) + t_{lo}$$

in the formula, $r_{hi}$ represents a maximum value of each variation segment b in the variation segment b in which the variation r is located, $r_{lo}$ represents a minimum value of each variation segment b in the variation segments b in which the variation r is located, $t_{hi}$ represents a maximum value in each collection cycle segment c, and $t_{lo}$ represents a minimum value in each collection cycle segments c.

Further, in S6, a calculation formula of the real-time particulate matter variation $r_2$ is:

$$r_2 = \left|\frac{d_1 - d_0}{d_0}\right|$$

in the formula, when the real-time particulate matter variation $r_2$ obtained through calculation is greater than 1, the real-time particulate matter variation $r_2$ is 1.

Further, in S4, a calculation formula of the real-time particulate matter collection interval time t4 is t_4=t_3/t_2.

Further, the variation r is evenly divided into several variation segments b from 0 to 1, and a difference between $r_{hi}$ and $r_{lo}$ in each variation segment b is less than or equal to 0.1.

Further, the shortest collection interval time $t_3$ of the particulate matter detector is greater than or equal to 1.5 seconds.

Further, the variation r is divided into 10 variation segments b.

Further, the initial collection duration $t_1$ is 10 seconds.

Compared with the related art, beneficial effects of the present invention are as follows. A variation of the concentration of the particulate matters in the air is calculated through a stepwise approximation method and table look-up to obtain a real-time collection cycle coefficient, and further obtain a real-time particulate matter collection interval time, so that the particulate matter detector can adjust a collection interval time in real time as the concentration of the particulate matters in the air changes. When a change in the concentration of the particulate matters in the air is small, an endurance capacity of the particulate matter detector is effectively improved through a long collection time interval; and when the concentration of the particulate matters in the air changes frequently, more accurate air particulate matter data is obtained through a short collection time interval.

DETAILED DESCRIPTION

The technical solutions in the present invention are clearly and completely described below with reference to the accompanying drawings. Apparently, the described embodiments are merely some rather than all of the embodiments of the present invention. All other embodiments obtained by a person of ordinary skill in the art based on the embodiments of the present invention without creative efforts shall fall within the protection scope of the present invention.

In the description of the present invention, it should be noted that, orientation or position relationships indicated by the terms "center", "on", "under", "left", "right", "vertical", "horizontal", "inner", "outer", and the like are orientation or position relationships shown based on the accompanying drawings, and are merely intended to conveniently describe the present invention and simplify the description, but are not intended to indicate or imply that a mentioned apparatus or element needs to have a particular direction or needs to be constructed and operated in a particular orientation. Therefore, such terms cannot be understood as a limitation on the present invention. In addition, the terms "first", "second", and "third" are merely used for a descriptive purpose, and cannot be understood as indicating or implying relative importance.

In the description of the present invention, it should be noted that, unless otherwise explicitly specified or defined, the terms "install", "connect", and "connection" should be understood in a broad sense. For example, the connection may be a fixed connection, a detachable connection, or an integral connection; or the connection may be a mechanical connection or an electrical connection; or the connection may be a direct connection, an indirect connection through an intermediary, or internal communication between two elements. A person of ordinary skill in the art may understand the specific meanings of the foregoing terms in the present invention according to specific situations. In addition, technical features involved in different implementations of the present invention described below may be combined together if there is no conflict.

Figure 1:
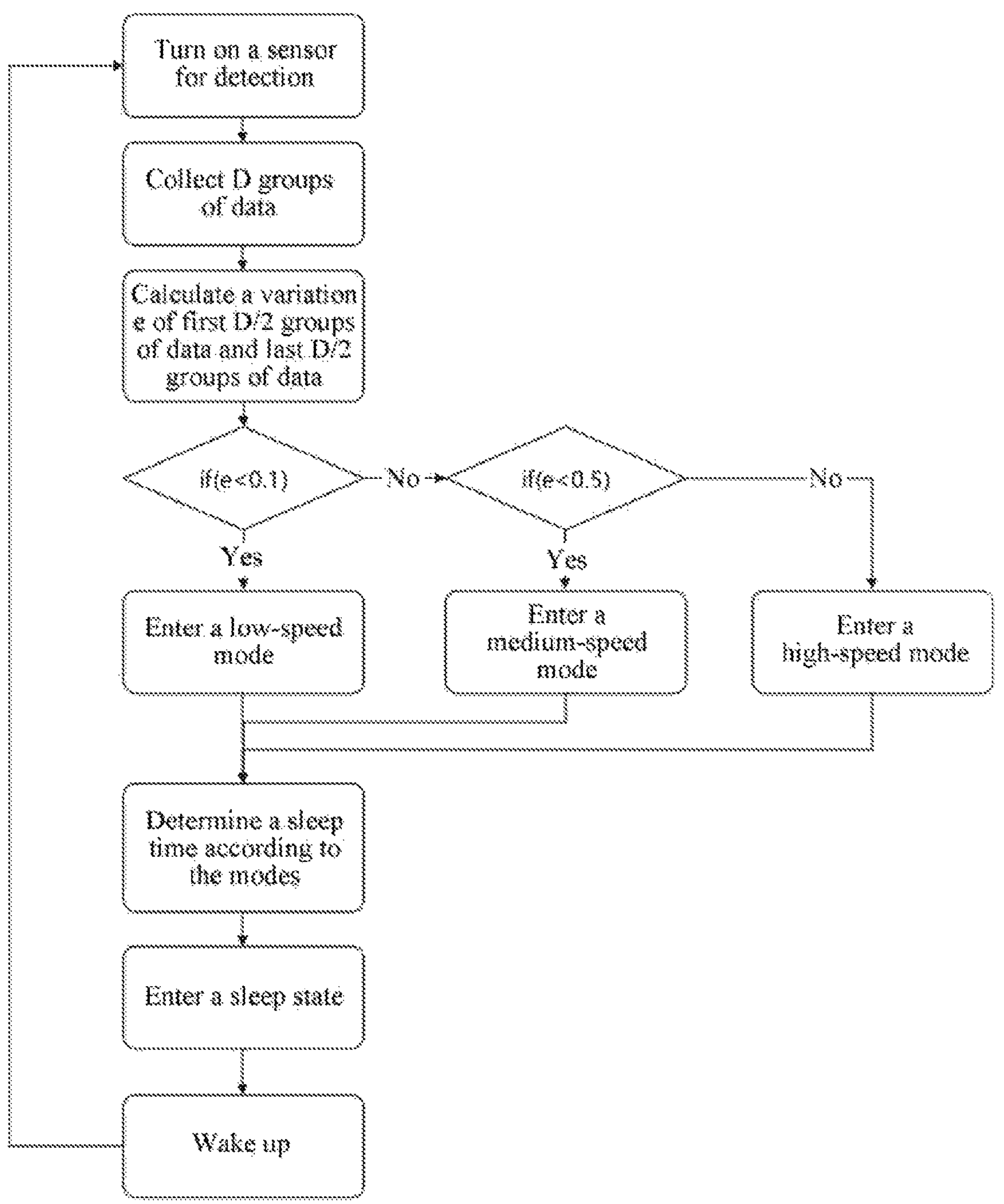
FIG. 1 is a flowchart of a method for controlling an air particulate matter collection rate.

As shown in FIG. 1, an energy-saving collection method for an air particulate matter detector is disclosed, which relates to a control method for adjusting a particulate matter collection rate according to a variation of particulate matters in the air. Main steps are as follows.

S1: Collect D groups of air particulate matter data through a sensor, where D is an even number.

S2: Calculate a variation e of the first D/2 groups of air particulate matter data and the last D/2 groups of air particulate matter data.

S3: Determine a value of the variation e.

S4: If the value of the variation e falls within an interval (0, 0.1), it means that the variation of the air particulate matter data is small, and the particulate matter detector enters a low-speed mode for detection; if the variation e falls within an interval [0.1, 0.5), it means that the variation of the air particulate matter data is moderate, and the particulate matter detector enters a medium-speed mode for detection; and if the variation e falls within an interval [0.5, +∞), it means that the variation of the air particulate matter data is great, and the particulate matter detector enters a high-speed mode for detection. Compared with the medium-speed mode, the high-speed mode has a larger quantity of detection times per unit time; and compared with the low-speed mode, the medium-speed mode has a larger quantity of detection times per unit time.

S5: After detection is completed, determine a sleep time of the particulate matter detector according to various modes such as the low-speed mode.

S6: The particulate matter detector enters a sleep state.

S7: Return to step S1 after the particulate matter detector is woken up.

The collection method for an air particulate matter detector discloses a control method for adjusting a particulate matter collection rate according to a variation of particulate matters in the air. This method requires a sleep state. During the sleep state, detection cannot be performed. Once a large change in a concentration of the particulate matters in the air occurs, the change cannot be detected. Simultaneously, there are only three detection modes: the high-speed mode, the medium-speed mode, and the low-speed mode. A few modes are set and the detection mode cannot be adjusted in real time. As a result, the energy consumption of the air particulate matter detector can be hardly reduced.

Figure 2:
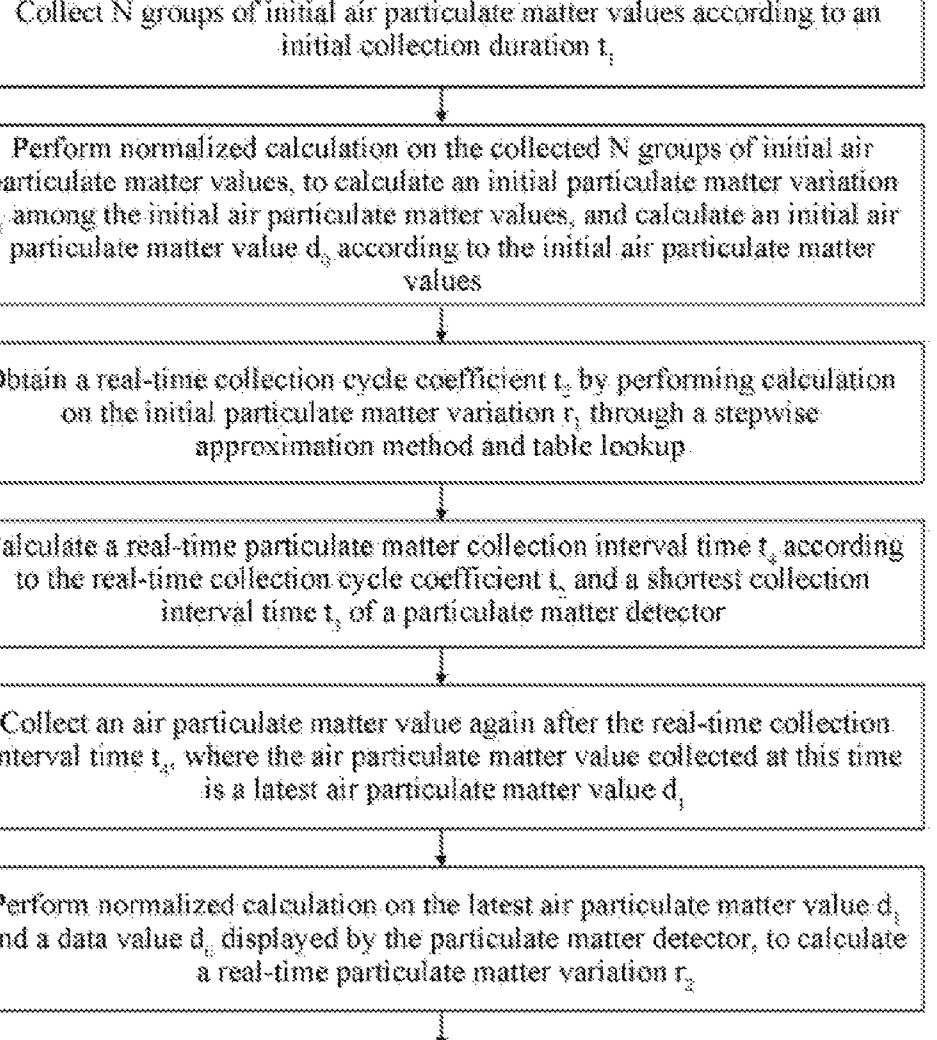
FIG. 2 is a flowchart of an energy-saving collection method for a particulate matter detector according to the present invention.

Therefore, as shown in FIG. 2, the present invention provides an energy-saving collection method for a particulate matter detector. Main steps are as follows:

S1: Collect N groups of initial air particulate matter values according to an initial collection duration $t_1$, where the initial collection duration $t_1$ may be 10 seconds.

S2: Perform normalized calculation on the collected N groups of initial air particulate matter values, to calculate an initial particulate matter variation $r_1$ among the initial air particulate matter values, where when N is an even number, normalized calculation is performed on the initial particulate matter variation $r_1$ using the following formula, $$r_1 = \left|\frac{a_1 - a_2}{a_1}\right|$$

in the formula, $a_1$ is an average value of the first N/2 groups of initial air particulate matter value data, and $a_2$ is an average value of the last N/2 groups of initial air particulate matter value data; and when N is an odd number, a first piece of data in the N groups of data is discarded, M groups of data is left, and normalized calculation is performed on the initial particulate matter variation $r_1$ using the following formula, $$r_1 = \left|\frac{a_3 - a_4}{a_3}\right|$$

in the formula, $a_3$ is an average value of the first M/2 groups of initial air particulate matter value data, and $a_4$ is an average value of the last M/2 groups of initial air particulate matter value data.

In addition, an initial air particulate matter value $d_0$ is calculated according to the initial air particulate matter values. In this case, the initial air particulate matter value $d_0$ is displayed on a display interface of the particulate matter detector, and a user can see air particulate matter concentration information in this case.

S3: Obtain a real-time collection cycle coefficient $t_2$ by performing calculation on the initial particulate matter variation $r_1$ through a stepwise approximation method and table lookup.

In detail, a specific method of the stepwise approximation method and table lookup is: defining the initial particulate matter variation $r_1$ as a variation r, and setting a table as shown in Table 1 to perform table lookup.

TABLE 1

Real-time collection cycle coefficient $t_2$ query comparison table

| Variation r | Collection cycle coefficient $t_2$ |
|---|---|
| (0.9, 1] | [0.89, 1] |
| (0.8, 0.9] | [0.78, 0.89] |
| (0.7, 0.8] | [0.67, 0.78] |
| (0.6, 0.7] | [0.56, 0.67] |
| (0.5, 0.6] | [0.45, 0.56] |
| (0.4, 0.5] | [0.23, 0.45] |
| (0.3, 0.4] | [0.05, 0.23] |
| (0.2, 0.3] | [0.012, 0.05] |
| (0.1, 0.2] | [0.01, 0.012] |
| (0, 0.1] | [0.008, 0.01] |

In this embodiment, in Table 1, the variation r is evenly divided into 10 variation segments b from 0 to 1, and each variation segment b has a different value range. In other embodiments, there may also be more than 10 variation segments b.

Each variation segment b is provided with a corresponding collection cycle segment c, and each collection cycle segment c also has a different value range; and a calculation formula using the stepwise approximation method is:

$$t_2 = \frac{t_{hi} - t_{lo}}{r_{hi} - r_{lo}}(r - r_{lo}) + t_{lo}$$

in the formula, $r_{hi}$ represents a maximum value of each variation segment b in the variation segments b in which the variation r is located, $r_{lo}$ represents a minimum value of each variation segment b in the variation segments b in which the variation r is located, $t_{hi}$ represents a maximum value in each collection cycle segment c, and $t_{lo}$ represents a minimum value in each collection cycle segment c. In this embodiment, a difference between $r_{hi}$ and $r_{lo}$ in each variation segment b is 0.1. In other embodiments, when a quantity of the variation segments b is more than 10, the difference between $r_{hi}$ and $r_{lo}$ in each variation segment b may be 0.08, 0.05, or any value within an interval (0, 0.1]. Through the stepwise approximation method, a degree of correlation between the variation r and the collection cycle coefficient $t_2$ may be higher, and an ideal collection cycle may be calculated more accurately according to the variation.

In this embodiment, if it is calculated that $r_1$ is 0.55 in S2, then when the real-time collection cycle coefficient $t_2$ is calculated, by querying Table 1, the segment (0.5, 0.6] is selected as the variation segment b, the corresponding collection cycle segment c is [0.45, 0.56], and these values are substituted in the calculation formula using the stepwise approximation method. Finally, $$t_2 = \frac{0.56 - 0.45}{0.6 - 0.5} \times (0.55 - 0.5) + 0.45 = 0.505$$

S4: Calculate a real-time particulate matter collection interval time $t_4$ according to the real-time collection cycle coefficient $t_2$ and a shortest collection interval time $t_3$ of the particulate matter detector, where the shortest collection interval time $t_3$ of the particulate matter detector is greater than or equal to 1.5 seconds. In this embodiment, the shortest collection interval time $t_3$ of the particulate matter detector is 1.5 seconds. A calculation formula of the real-time particulate matter collection interval time $t_4$ is:

$$t_4 = \frac{t_3}{t_2}$$

In this embodiment, when the real-time collection cycle coefficient $t_2$ is 0.505, the real-time particulate matter collection interval time $t_4$=1.5/0.505≈2.97 seconds.

S5: Collect an air particulate matter value again after the real-time collection interval time $t_4$, where the air particulate matter value collected at this time is a latest air particulate matter value $d_1$.

S6: Perform normalized calculation on the latest air particulate matter value $d_1$ and a data value $d_0$ displayed by the particulate matter detector, to calculate a real-time particulate matter variation $r_2$. In S6, a normalized calculation formula of the real-time particulate matter variation $r_2$ is:

$$r_2 = \left|\frac{d_1 - d_0}{d_0}\right|$$

In the formula, when the real-time particulate matter variation $r_2$ obtained through calculation is greater than 1, the real-time particulate matter variation $r_2$ is 1.

S7: Obtain a new real-time collection cycle coefficient $t_2$ by performing calculation on the real-time particulate matter variation $r_2$ again through the calculation formula using the stepwise approximation method and querying Table 1.

$$t_2 = \frac{t_{hi} - t_{lo}}{r_{hi} - r_{lo}}(r - r_{lo}) + t_{lo}$$

In a process of calculating the real-time collection cycle coefficient $t_2$, the real-time particulate matter variation $r_2$ is defined as the variation r. In this case, the latest air particulate matter value $d_1$ is assigned to the initial air particulate matter value $d_0$. In addition, the latest air particulate matter value $d_1$ is displayed on the display interface of the particulate matter detector, and the user can see latest air particulate matter concentration information.

S8: Repeat the steps from S4 to S7 until the particulate matter detector is turned off.

According to the present invention, calculation is performed on the variation of the particulate matters through the stepwise approximation method and table look-up to obtain the real-time collection cycle coefficient, and further obtain the real-time particulate matter collection interval time, so that the particulate matter detector can adjust the collection interval time in real time as the concentration of the particulate matters in the air changes. When a change in the concentration of the particulate matters in the air is small, an endurance capacity of the particulate matter detector is effectively improved through a long collection time interval; and when the concentration of the particulate matters in the air changes frequently, more accurate air particulate matter data is obtained through a short collection time interval.

It should be emphasized that, the above embodiments are merely exemplary embodiments of the present invention, and are not intended to limit the present invention in any form. Any simple variation, equivalent change, and modification made to the above embodiments according to the technical essence of the present invention still fall within the scope of the technical solutions of the present invention.

The invention claimed is:

1. A collection method for a particulate matter detector, comprising the following steps:

S1, collecting N groups of initial air particulate matter values according to an initial collection duration $t_1$;

S2, performing normalized calculation on the collected N groups of initial air particulate matter values, to calculate an initial particulate matter variation $r_1$ among the initial air particulate matter values, and calculating an initial air particulate matter value $d_0$ according to the initial air particulate matter values;

S3, obtaining a real-time collection cycle coefficient $t_2$ by performing calculation on the initial particulate matter variation $r_1$ through a stepwise approximation method and table lookup;

S4, calculating a real-time particulate matter collection interval time $t_4$ according to the real-time collection cycle coefficient $t_2$ and a shortest collection interval time $t_3$ of the particulate matter detector;

S5, collecting an air particulate matter value again after the real-time collection interval time $t_4$, where the air particulate matter value collected at this time is a latest air particulate matter value $d_1$;

S6, performing normalized calculation on the latest air particulate matter value $d_1$ and a data value $d_0$ displayed by the particulate matter detector, to calculate a real-time particulate matter variation $r_2$;

S7, obtaining a new real-time collection cycle coefficient $t_2$ by performing calculation on the real-time particulate matter variation $r_2$ through the stepwise approximation method and table lookup, wherein the latest air particulate matter value $d_1$ is assigned to the initial air particulate matter value $d_0$ in this case; and S8, repeating the steps from S4 to S7.

2. The collection method for a particulate matter detector according to claim 1, wherein in S2, when N is an even number, the initial particulate matter variation $r_1$ is calculated using the following formula, $$r_1 = \left|\frac{a_1 - a_2}{a_1}\right|$$

in the formula, $a_1$ is an average value of the first N/2 groups of initial air particulate matter value data, and $a_2$ is an average value of the last N/2 groups of initial air particulate matter value data.

3. The collection method for a particulate matter detector according to claim 1, wherein in S2, when N is an odd number, a first piece of data in the N groups of data is discarded, M groups of data is left, and the initial particulate matter variation $r_1$ is calculated using the following formula, $$r_1 = \left|\frac{a_3 - a_4}{a_3}\right|$$

in the formula, $a_3$ is an average value of the first M/2 groups of initial air particulate matter value data, and $a_4$ is an average value of the last M/2 groups of initial air particulate matter value data.

4. The collection method for a particulate matter detector according to claim 1, wherein a specific method of the stepwise approximation method and table lookup in S3 and S7 is: defining the initial particulate matter variation $r_1$ or the real-time particulate matter variation $r_2$ as a variation r, setting a table, and dividing the variation r in the table into several variation segments b from 0 to 1, wherein each variation segment b has a different value range; each variation segment b is provided with a corresponding collection cycle segment c, and each collection cycle segment c also has a different value range; and a calculation formula using the stepwise approximation method is:

$$t_2 = \frac{t_{hi} - t_{lo}}{r_{hi} - r_{lo}}(r - r_{lo}) + t_{lo}$$

in the formula, $r_{hi}$ represents a maximum value of each variation segment b in the variation segment b in which the variation r is located, $r_{lo}$ represents a minimum value of each variation segment b in the variation segments b in which the variation r is located, $t_{hi}$ represents a maximum value in each collection cycle segment c, and $t_{lo}$ represents a minimum value in each collection cycle segments c.

5. The collection method for a particulate matter detector according to claim 4, wherein the variation r is evenly divided into several variation segments b from 0 to 1, and a difference between $r_{hi}$ and $r_{lo}$ in each variation segment b is less than or equal to 0.1.

6. The collection method for a particulate matter detector according to claim 4, wherein the variation r is divided into 10 variation segments b.

7. The collection method for a particulate matter detector according to claim 1, wherein in S6, a calculation formula of the real-time particulate matter variation $r_2$ is:

$$r_2 = \left|\frac{d_1 - d_0}{d_0}\right|$$

in the formula, when the real-time particulate matter variation $r_2$ obtained through calculation is greater than 1, the real-time particulate matter variation $r_2$ is 1.

8. The collection method for a particulate matter detector according to claim 1, wherein in S4, a calculation formula of the real-time particulate matter collection interval time $t_4$ is $$t_4 = \frac{t_3}{t_2}.$$

9. The collection method for a particulate matter detector according to claim 8, wherein the shortest collection interval time $t_3$ of the particulate matter detector is greater than or equal to 1.5 seconds.

10. The collection method for a particulate matter detector according to claim 1, wherein the initial collection duration $t_1$ is 10 seconds.

* * * * *